US012746083B2

(12) United States Patent
(10) Patent No.: US 12,746,083 B2
(45) Date of Patent: Sep. 29, 2026
Hazan et al.

(54) CONTROL SYSTEM AND METHOD FOR ROBOTIC SYSTEMS

(71) Applicant: MOMENTIS SURGICAL LTD., Or Yehuda (IL)

(72) Inventors: Ben Hazan, Or Yehuda (IL); Efrat Milman, Or Yehuda (IL); Inbal Regev, Or Yehuda (IL); Shay Katz, Or Yehuda (IL); Ofer Fishman, Or Yehuda (IL)

(73) Assignee: MOMENTIS SURGICAL LTD., Or Yehuda (IL)

( * ) Notice: Subject to any disclaimer, the term of this patent is extended or adjusted under 35 U.S.C. 154(b) by 0 days.

(21) Appl. No.: 18/838,626

(22) PCT Filed: Feb. 16, 2023

(86) PCT No.: PCT/IL2023/050167
§ 371 (c)(1),
(2) Date: Aug. 15, 2024

(87) PCT Pub. No.: WO2023/157002
PCT Pub. Date: Aug. 24, 2023

(65) Prior Publication Data

US 2025/0143820 A1 May 8, 2025

Related U.S. Application Data

(60) Provisional application No. 63/334,201, filed on Apr. 25, 2022, provisional application No. 63/311,059, filed on Feb. 17, 2022.

(51) Int. Cl.
*A61B 34/37* (2016.01)
*A61B 34/00* (2016.01)
(Continued)

(52) U.S. Cl.
CPC .............. *A61B 34/37* (2016.02); *A61B 34/30* (2016.02); *A61B 34/74* (2016.02); *B25J 13/06* (2013.01);
(Continued)

(58) Field of Classification Search
CPC ......... A61B 34/37; A61B 34/30; A61B 34/74; A61B 34/76; A61B 2034/305;
(Continued)

(56) References Cited

U.S. PATENT DOCUMENTS 9,517,106 B2 * 12/2016 Hourtash ............... A61B 34/25
10,145,747 B1 12/2018 Lin et al.
(Continued)

FOREIGN PATENT DOCUMENTS

WO 2020171836 A1 8/2020
WO 2021252407 A1 12/2021

*Primary Examiner* — Sohana Tanju Khayer
(74) *Attorney, Agent, or Firm* — S. J. Intellectual Property Limited

(57) ABSTRACT

The presently disclosed subject matter aims to a system and method including a processing circuitry configured to: obtain: (a) a current input control configuration of at least one input control of one or more input controls, and (b) a current mechanical arm configuration of at least one mechanical arm of one or more mechanical arms; identify a misalignment between at least one input control of the one or more input controls and its respective at least one mechanical arm of the one or more mechanical arms by comparing the current input control configuration and the current mechanical arm configuration of the at least one input control of the one or more input controls and its respective at least one mechanical arm of the one or more mechanical arms; and, upon identification of the misalignment, perform an action.

21 Claims, 8 Drawing Sheets

(51) Int. Cl.
*A61B 34/30* (2016.01)
*B25J 13/06* (2006.01)

(52) U.S. Cl.
CPC ... *A61B 2034/305* (2016.02); *A61B 2034/742* (2016.02); *A61B 34/76* (2016.02); *G05B 2219/45117* (2013.01)

(58) Field of Classification Search
CPC .... A61B 2034/742; A61B 34/71; B25J 13/06; B25J 9/1689; G05B 2219/45117
See application file for complete search history.

(56) References Cited

U.S. PATENT DOCUMENTS

| | | | | |
|---|---|---|---|---|
| 2004/0254680 | A1 | 12/2004 | Sunaoshi | |
| 2005/0251110 | A1 | 11/2005 | Nixon | |
| 2015/0314451 | A1 | 11/2015 | Nixon | |
| 2017/0156808 | A1* | 6/2017 | Auld | A61B 34/70 |
| 2017/0360519 | A1* | 12/2017 | Yorimoto | B25J 9/1689 |
| 2019/0105117 | A1 | 4/2019 | Brisson | |
| 2019/0107454 | A1* | 4/2019 | Lin | A61B 1/00149 |
| 2020/0230815 | A1 | 7/2020 | Nikovski et al. | |
| 2022/0134555 | A1* | 5/2022 | Peine | B25J 9/1653 700/254 |
| 2022/0241962 | A1* | 8/2022 | Nguyen | B25J 9/1697 |
| 2022/0250242 | A1* | 8/2022 | Suresh | A61B 34/10 |
| 2023/0260640 | A1* | 8/2023 | Dierksen | A61B 34/37 606/1 |
| 2023/0277257 | A1* | 9/2023 | Terry | A61B 90/37 606/1 |
| 2023/0286169 | A1* | 9/2023 | Imanishi | G05B 19/41825 |
| 2024/0004369 | A1* | 1/2024 | Agrawal | A61B 34/25 |
| 2024/0033025 | A1* | 2/2024 | Yilmaz | A61B 34/76 |
| 2024/0033930 | A1* | 2/2024 | Narasaki | G06T 17/00 |
| 2024/0091941 | A1* | 3/2024 | Naramura | B25J 19/023 |
| 2024/0399573 | A1* | 12/2024 | Ikeguchi | B25J 9/1697 |
| 2025/0009434 | A1* | 1/2025 | Ye | A61B 34/20 |

* cited by examiner

CONTROL SYSTEM AND METHOD FOR ROBOTIC SYSTEMS

TECHNICAL FIELD

The present invention relates to the field of robotic surgery.

BACKGROUND

Robot-assisted surgeries are surgical procedures performed using robotic systems. These systems, which typically include one or more input controls (or controllers) configured to control the movement of one or more respective surgical mechanical arms during system operation, were developed to try and overcome the limitations of pre-existing minimally-invasive surgical procedures, as well as to enhance the capabilities of surgeons performing open surgery.

Although they have allowed a major leap forward in the way surgical procedures are performed today, existing robotic systems are prone to misalignment conditions, in which the input controls (or controllers) and their respective surgical mechanical arms fail to synchronize in their operation and movement. These conditions can jeopardize the surgical procedure's chances of success and pose an actual risk to the patient's safety and health.

Thus, there is a need in the art for a new control system for robotic systems.

GENERAL DESCRIPTION

In accordance with a first aspect of the presently disclosed subject matter, there is provided a control system for a robotic system consisting of one or more input controls, each including a plurality of input control sections sequentially coupled by input control joints, and one or more mechanical arms, each associated with a respective input control of the one or more input controls and includes a plurality of segments coupled to one another, wherein each segment is configured to imitate an angle of a respective pair of input control sections, coupled by an input control joint, the control system comprising a processing circuitry configured to: obtain: (a) a current input control configuration of at least one input control of the one or more input controls, and (b) a current mechanical arm configuration of at least one mechanical arm of the one or more mechanical arms; wherein: (i) one or more segments of the plurality of segments define the current mechanical arm configuration, and (ii) one or more input control angles of one or more input control joints of the input control joints define the current input control configuration; identify a misalignment between at least one input control of the one or more input controls and its respective at least one mechanical arm of the one or more mechanical arms by comparing the current input control configuration and the current mechanical arm configuration of the at least one input control of the one or more input controls and its respective at least one mechanical arm of the one or more mechanical arms; and, upon identification of the misalignment, perform an action.

In some cases, the action includes one or more of: (a) providing a user of the system with an indication of the misalignment, (b) causing movement of at least one segment of the at least one mechanical arm to at least reduce the misalignment between the current input control configuration of the input control and the current mechanical arm configuration of the mechanical arm, or (c) instructing the user to move at least one joint of the at least one input control to at least reduce the misalignment between the current input control configuration of the input control and the current mechanical arm configuration of the mechanical arm.

In some cases, the identify and the perform are performed when the at least one input control of the one or more input controls and its respective at least one mechanical arm of the one or more mechanical arms are in a pause or upon resume mode, in which the input control and the mechanical arm are configured to maintain their configuration.

In some cases, each input control angle of the one or more input control angles of the at least one input control is an angle between two adjacent sections of the plurality of input control sections, coupled by an input control joint of the input control joints.

In some cases, the configuration of the at least one mechanical arm is determined by measuring a tension found on at least one cable connecting the mechanical arm to a respective motor.

In some cases, the configuration of the at least one mechanical arm is determined by measuring the operation of a respective motor connected to the at least one mechanical arm.

In some cases, the misalignment between the at least one input control of the one or more input controls and its respective at least one mechanical arm of the one or more mechanical arms is identified upon any pair of respective angles of the one or more input control angles and the one or more angles imitated by respective segments of the one or more mechanical arms meeting a misalignment condition.

In some cases, the misalignment condition is that a difference between the respective angles exceeds a tolerance threshold, or that the angles of the pair are not equal.

In some cases, the action is causing movement of the at least one segment, and wherein the movement is performed upon an angular difference between the at least one input control and its respective at least one mechanical arm being above a low threshold and below a high threshold.

In some cases, the action is providing a user with an indication of the misalignment, and wherein the action is performed upon an angular difference between the at least one input control and its respective at least one mechanical arm being above a low threshold.

In some cases, the angular difference is determined based on at least one joint angular difference being the angular difference between at least one input control joint and its respective at least one segment.

In some cases, the action is selected from a plurality of possible actions based on a type of tool coupled to a distal end of the at least one mechanical arm.

In some cases, the action includes providing haptic feedback using a haptic feedback mechanism comprised within the at least one input control.

In some cases, misalignment between the at least one input control of the one or more input controls and its respective at least one mechanical arm of the one or more mechanical arms is due to the at least one mechanical arm contacting an object preventing the mechanical arm from moving further, while the input control is still in motion.

In some cases, the object is a tissue.

In some cases, the misalignment between the at least one input control of the one or more input controls and its respective at least one mechanical arm of the one or more mechanical arms is due to movement of the at least one mechanical arm independently of the at least one input control.

In some cases, the misalignment between the at least one input control of the one or more input controls and its respective at least one mechanical arm of the one or more mechanical arms is due to physical movement limitations associated with the at least one mechanical arm.

In some cases, the misalignment between the at least one input control of the one or more input controls and its respective at least one mechanical arm of the one or more mechanical arms is due to movement of the at least one input control while in a pause mode.

In some cases, the misalignment between the at least one input control of the one or more input controls and its respective at least one mechanical arm of the one or more mechanical arms is due to use of an emergency button associated with the at least one input control and its respective at least one mechanical arm, wherein upon pressing of the emergency button the at least one input control and its respective at least one mechanical arm are configured to maintain their configuration.

In some cases, the misalignment between the at least one input control of the one or more input controls and its respective at least one mechanical arm of the one or more mechanical arms is due to an initial configuration of the at least one input control and the at least one mechanical arm.

In some cases, the misalignment between the at least one input control of the one or more input controls and its respective at least one mechanical arm of the one or more mechanical arms is due to one or more arm malfunctions.

In accordance with a second aspect of the presently disclosed subject matter, there is provided a control system for a robotic system including one or more input controls, each including a plurality of input control sections sequentially coupled by input control joints, the control system comprising a processing circuitry configured to: obtain: (a) a previous input control configuration of at least one input control of the one or more input controls, and (b) a current input control configuration of the at least one input control; wherein each configuration of the at least one input control is defined by one or more input control angles of the one or more input control joints of the input control joints; identify a misalignment between the previous input control configuration and the current input control configuration of the at least one mechanical arm by comparing the configurations; and, upon identification of the misalignment, perform an action.

In some cases, the action includes one or more of: (a) providing a user of the system with an indication of the misalignment, or (b) instructing the user to move at least one joint of the at least one input control to at least reduce the misalignment between the current input control configuration of the input control and the previous input control configuration of the input control.

In some cases, the identify and the perform are performed when the at least one input control is in a pause or upon resume mode in which the input control is configured to maintain its configuration.

In some cases, each input control angle of the one or more input control angles of the at least one input control is an angle between two adjacent sections of the plurality of input control sections, coupled by an input control joint of the input control joints.

In some cases, the misalignment between the previous and current configurations of the at least one input control of the one or more input controls is identified upon any pair of respective angles of the previous and current configurations meeting a misalignment condition.

In some cases, the misalignment condition is a difference between the angles of the pair exceed a tolerance threshold, or that the angles of the pair are not equal.

In some cases, the action includes providing haptic feedback using a haptic feedback mechanism comprised within the at least one input control.

In accordance with a third aspect of the presently disclosed subject matter, there is provided a control method for a robotic system consisting of one or more input controls, each including a plurality of input control sections sequentially coupled by input control joints, and one or more mechanical arms, each associated with a respective input control of the one or more input controls and includes a plurality of segments coupled to one another, wherein each segment is configured to imitate an angle of a respective pair of input control sections, coupled by an input control joint, the control method comprising: obtaining: (a) a current input control configuration of at least one input control of the one or more input controls, and (b) a current mechanical arm configuration of at least one mechanical arm of the one or more mechanical arms; wherein: (i) one or more segments of the plurality of segments define the current mechanical arm configuration, and (ii) one or more input control angles of one or more input control joints of the input control joints define the current input control configuration; identifying a misalignment between at least one input control of the one or more input controls and its respective at least one mechanical arm of the one or more mechanical arms by comparing the current input control configuration and the current mechanical arm configuration of the at least one input control of the one or more input controls and its respective at least one mechanical arm of the one or more mechanical arms; and, upon identification of the misalignment, performing an action.

In some cases, the action includes one or more of: (a) providing a user with an indication of the misalignment, (b) causing movement of at least one segment of the at least one mechanical arm to at least reduce the misalignment between the current input control configuration of the input control and the current mechanical arm configuration of the mechanical arm, or (c) instructing the user to move at least one joint of the at least one input control to at least reduce the misalignment between the current input control configuration of the input control and the current mechanical arm configuration of the mechanical arm.

In some cases, the identifying and the performing are performed when the at least one input control of the one or more input controls and its respective at least one mechanical arm of the one or more mechanical arms are in a pause or upon resume mode, in which the input control and the mechanical arm are configured to maintain their configuration.

In some cases, each input control angle of the one or more input control angles of the at least one input control is an angle between two adjacent sections of the plurality of input control sections, coupled by an input control joint of the input control joints.

In some cases, the configuration of the at least one mechanical arm is determined by measuring a tension found on at least one cable connecting the mechanical arm to a respective motor.

In some cases, the configuration of the at least one mechanical arm is determined by measuring the operation of a respective motor connected to the at least one mechanical arm.

In some cases, the misalignment between the at least one input control of the one or more input controls and its respective at least one mechanical arm of the one or more mechanical arms is identified upon any pair of respective angles of the one or more input control angles and the one or more angles imitated by respective segments of the one or more mechanical arms meeting a misalignment condition.

In some cases, the misalignment condition is that a difference between the respective angles exceeds a tolerance threshold, or that the angles of the pair are not equal.

In some cases, the action is causing movement of the at least one segment, and wherein the movement is performed upon an angular difference between the at least one input control and its respective at least one mechanical arm being above a low threshold and below a high threshold.

In some cases, the action is providing a user with an indication of the misalignment, and wherein the action is performed upon an angular difference between the at least one input control and its respective at least one mechanical arm being above a low threshold.

In some cases, the angular difference is determined based on at least one joint angular difference being the angular difference between at least one input control joint and its respective at least one segment.

In some cases, the action is selected from a plurality of possible actions based on a type of tool coupled to a distal end of the at least one mechanical arm.

In some cases, the action includes providing haptic feedback using a haptic feedback mechanism comprised within the at least one input control.

In some cases, the misalignment between the at least one input control of the one or more input controls and its respective at least one mechanical arm of the one or more mechanical arms is due to the at least one mechanical arm contacting an object preventing the mechanical arm from moving further, while the input control is still in motion.

In some cases, the object is a tissue.

In some cases, the misalignment between the at least one input control of the one or more input controls and its respective at least one mechanical arm of the one or more mechanical arms is due to movement of the at least one mechanical arm independently of the at least one input control.

In some cases, the misalignment between the at least one input control of the one or more input controls and its respective at least one mechanical arm of the one or more mechanical arms is due to physical movement limitations associated with the at least one mechanical arm.

In some cases, the misalignment between the at least one input control of the one or more input controls and its respective at least one mechanical arm of the one or more mechanical arms is due to movement of the at least one input control while in a pause mode.

In some cases, the misalignment between the at least one input control of the one or more input controls and its respective at least one mechanical arm of the one or more mechanical arms is due to use of an emergency button associated with the at least one input control and its respective at least one mechanical arm, wherein upon pressing of the emergency button the at least one input control and its respective at least one mechanical arm are configured to maintain their configuration.

In some cases, the misalignment between the at least one input control of the one or more input controls and its respective at least one mechanical arm of the one or more mechanical arms is due to an initial configuration of the at least one input control and the at least one mechanical arm.

In some cases, the misalignment between the at least one input control of the one or more input controls and its respective at least one mechanical arm of the one or more mechanical arms is due to one or more arm malfunctions.

In accordance with a fourth aspect of the presently disclosed subject matter, there is provided a control method for a robotic system including one or more input controls, each including a plurality of input control sections sequentially coupled by input control joints, the control method comprising: obtaining: (a) a previous input control configuration of at least one input control of the one or more input controls, and (b) a current input control configuration of the at least one input control; wherein each configuration of the at least one input control is defined by one or more input control angles of the one or more input control joints of the input control joints; identifying a misalignment between the previous input control configuration and the current input control configuration of the at least one mechanical arm by comparing the configurations; and, upon identification of the misalignment, performing an action.

In some cases, the action includes one or more of: (a) providing with an indication of the misalignment, or (b) instructing the user to move at least one joint of the at least one input control to at least reduce the misalignment between the current input control configuration of the input control and the previous input control configuration of the input control.

In some cases, the identifying and the performing are performed when the at least one input control is in a pause or upon resume mode in which the input control is configured to maintain its configuration.

In some cases, each input control angle of the one or more input control angles of the at least one input control is an angle between two adjacent sections of the plurality of input control sections, coupled by an input control joint of the input control joints.

In some cases, the misalignment between the previous and current configurations of the at least one input control of the one or more input controls is identified upon any pair of respective angles of the previous and current configurations meeting a misalignment condition.

In some cases, the misalignment condition is a difference between the angles of the pair exceed a tolerance threshold, or that the angles of the pair are not equal.

In some cases, the action includes providing haptic feedback using a haptic feedback mechanism comprised within the at least one input control.

In accordance with a fifth aspect of the presently disclosed subject matter, there is provided a non-transitory computer readable storage medium having computer readable program code embodied therewith, the computer readable program code, executable by at least one processor to perform a control method, the method comprising: obtaining: (a) a current input control configuration of at least one input control of the one or more input controls, and (b) a current mechanical arm configuration of at least one mechanical arm of the one or more mechanical arms; wherein: (i) one or more segments of the plurality of segments define the current mechanical arm configuration, and (ii) one or more input control angles of one or more input control joints of the input control joints define the current input control configuration; identifying a misalignment between at least one input control of the one or more input controls and its respective at least one mechanical arm of the one or more mechanical arms by comparing the current input control configuration and the current mechanical arm configuration of the at least one input control of the one or more input controls and its respective at least one mechanical arm of the one or more mechanical arms; and, upon identification of the misalignment, performing an action.

In accordance with a sixth aspect of the presently disclosed subject matter, there is provided a non-transitory computer readable storage medium having computer readable program code embodied therewith, the computer readable program code, executable by at least one processor to perform a control method, the method comprising: obtaining: (a) a previous input control configuration of at least one input control of the one or more input controls, and (b) a current input control configuration of the at least one input control; wherein each configuration of the at least one input control is defined by one or more input control angles of the one or more input control joints of the input control joints; identifying a misalignment between the previous input control configuration and the current input control configuration of the at least one mechanical arm by comparing the configurations; and, upon identification of the misalignment, performing an action.

BRIEF DESCRIPTION OF THE DRAWINGS

In order to understand the presently disclosed subject matter and to see how it may be carried out in practice, the subject matter will now be described, by way of non-limiting examples only, with reference to the accompanying drawings, in which.

DETAILED DESCRIPTION

Figure 1A:
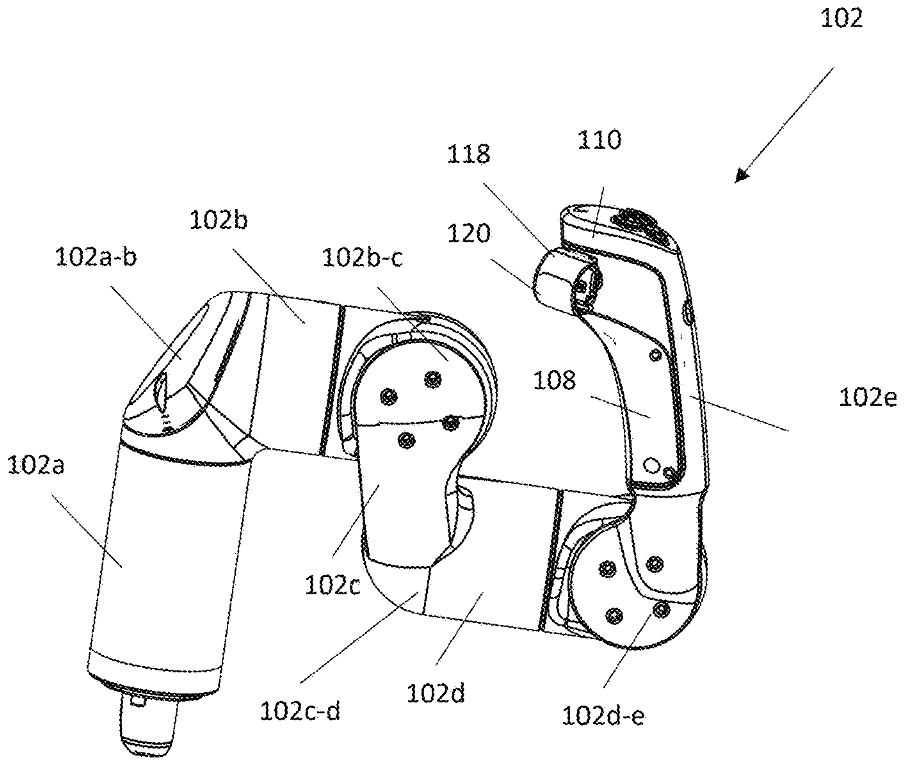
FIGS. 1A to 1C are schematic illustrations of components of a robotic system on which a control system for robotic systems operates, in accordance with the presently disclosed subject matter.

In the following detailed description, numerous specific details are set forth in order to provide a thorough understanding of the presently disclosed subject matter. However, it will be understood by those skilled in the art that the presently disclosed subject matter may be practiced without these specific details. In other instances, well-known methods, procedures, and components have not been described in detail so as not to obscure the presently disclosed subject matter.

In the drawings and descriptions set forth, identical reference numerals indicate those components that are common to different embodiments or configurations.

Unless specifically stated otherwise, as apparent from the following discussions, it is appreciated that throughout the specification discussions utilizing terms such as "obtaining". "identifying", "performing", "providing" "moving", "instructing" or the like, include action and/or processes of a computer that manipulate and/or transform data into other data, said data represented as physical quantities, e.g., such as electronic quantities, and/or said data representing the physical objects. The terms "computer", "processor", "processing resource", "processing circuitry", and "controller" should be expansively construed to cover any kind of electronic device with data processing capabilities, including, by way of non-limiting example, a personal desktop/laptop computer, a server, a computing system, a communication device, a smartphone, a tablet computer, a smart television, a processor (e.g. digital signal processor (DSP), a microcontroller, a field programmable gate array (FPGA), an application specific integrated circuit (ASIC), etc.), a group of multiple physical machines sharing performance of various tasks, virtual servers co-residing on a single physical machine, any other electronic computing device, and/or any combination thereof.

The operations in accordance with the teachings herein may be performed by a computer specially constructed for the desired purposes or by a general-purpose computer specially configured for the desired purpose by a computer program stored in a non-transitory computer readable storage medium. The term "non-transitory" is used herein to exclude transitory, propagating signals, but to otherwise include any volatile or non-volatile computer memory technology suitable to the application.

As used herein, the phrase "for example," "such as", "for instance" and variants thereof describe non-limiting embodiments of the presently disclosed subject matter. Reference in the specification to "one case", "some cases", "other cases" or variants thereof means that a particular feature, structure or characteristic described in connection with the embodiment(s) is included in at least one embodiment of the presently disclosed subject matter. Thus, the appearance of the phrase "one case", "some cases", "other cases" or variants thereof does not necessarily refer to the same embodiment(s).

It is appreciated that, unless specifically stated otherwise, certain features of the presently disclosed subject matter, which are, for clarity, described in the context of separate embodiments, may also be provided in combination in a single embodiment. Conversely, various features of the presently disclosed subject matter, which are, for brevity, described in the context of a single embodiment, may also be provided separately or in any suitable sub-combination.

Figure 2:
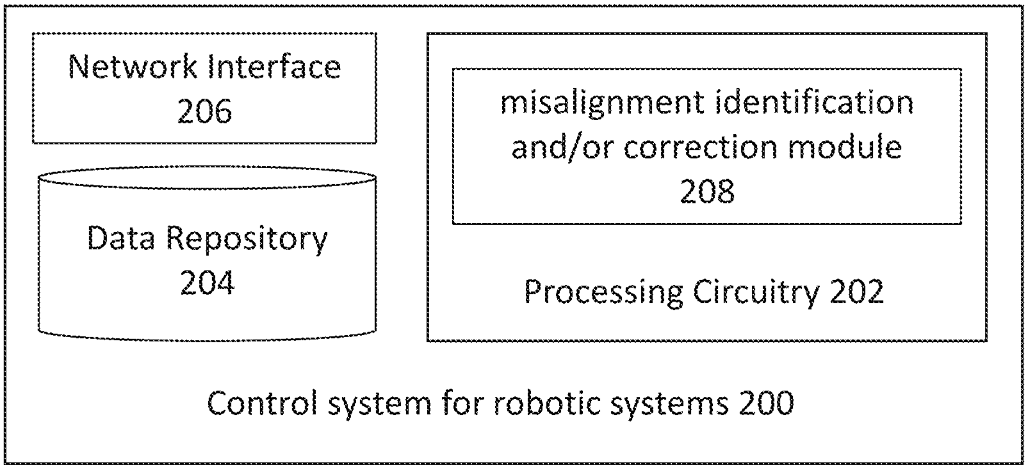
FIG. 2 is a block diagram schematically illustrating one example of a control system for robotic systems, in accordance with the presently disclosed subject matter.
Figure 3:
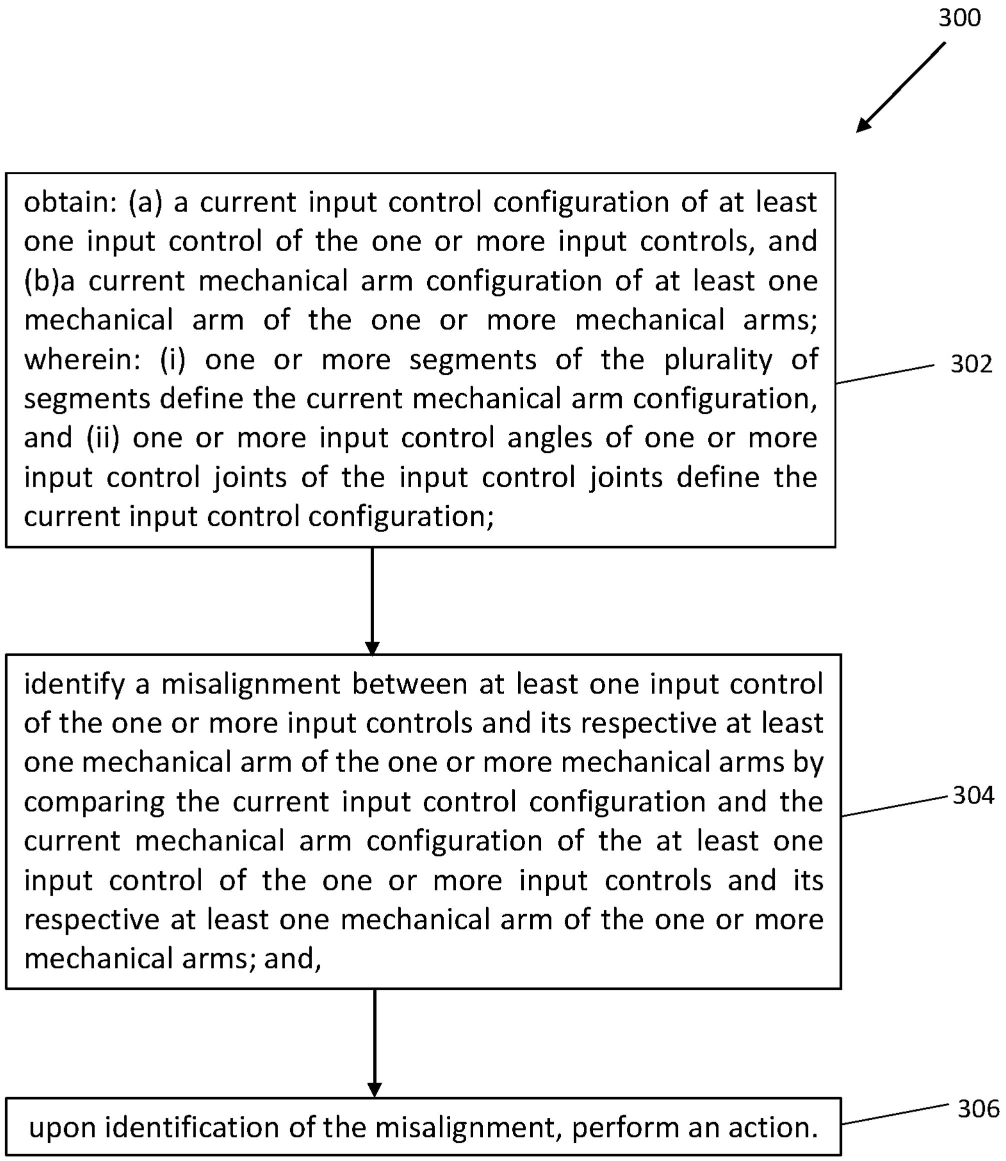
FIG. 3 is a flowchart illustrating one example of a sequence of operations carried out by a control system for robotic systems, in accordance with the presently disclosed subject matter.
Figure 5:
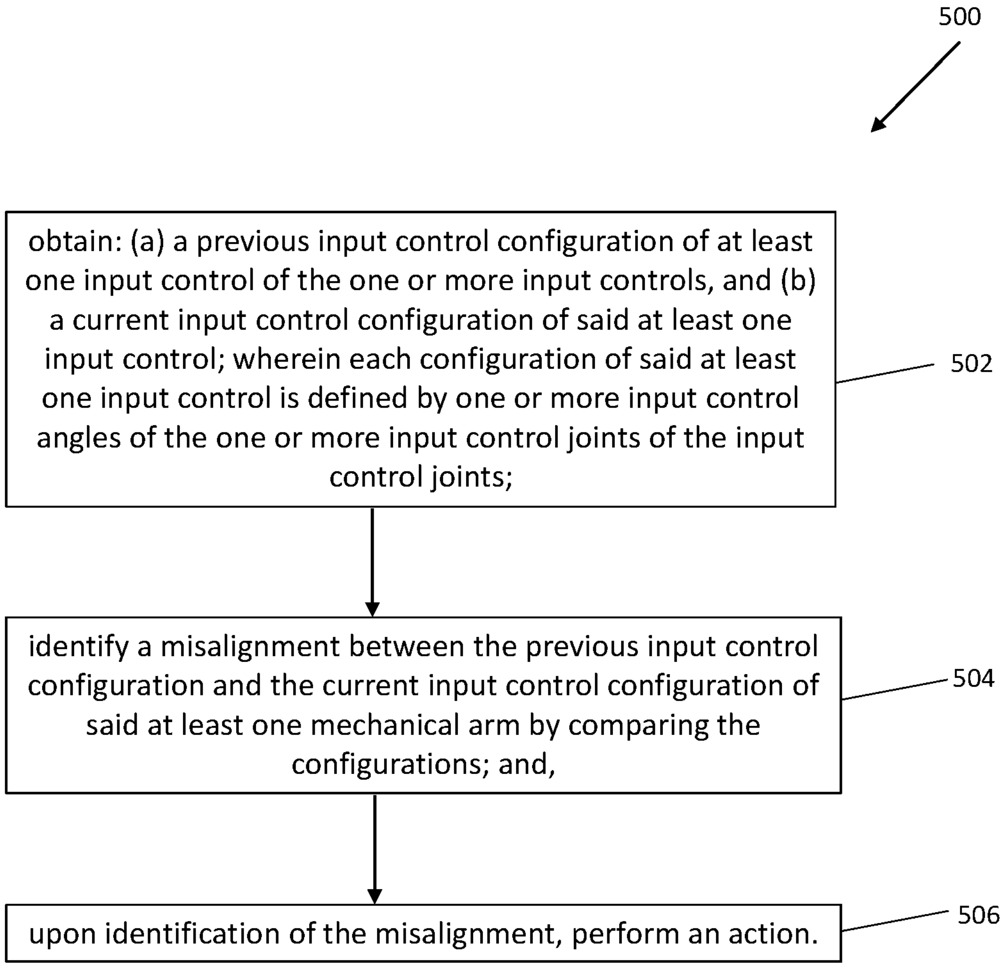

In embodiments of the presently disclosed subject matter, fewer, more and/or different stages than those shown in FIGS. 3 and 5 may be executed. In embodiments of the presently disclosed subject matter one or more stages illustrated in FIGS. 3 and 5 may be executed in a different order and/or one or more groups of stages may be executed simultaneously. FIGS. 1A to 1C and FIG. 2 illustrate a general schematic of the system architecture in accordance with an embodiment of the presently disclosed subject matter. Each module in FIG. 2 can be made up of any combination of software, hardware and/or firmware that performs the functions as defined and explained herein. The modules in FIG. 2 may be centralized in one location or dispersed over more than one location. In other embodiments of the presently disclosed subject matter, the system may comprise fewer, more, and/or different modules than those shown in FIG. 2.

Any reference in the specification to a method should be applied mutatis mutandis to a system capable of executing the method and should be applied mutatis mutandis to a non-transitory computer readable medium that stores instructions that once executed by a computer result in the execution of the method.

Any reference in the specification to a system should be applied mutatis mutandis to a method that may be executed by the system and should be applied mutatis mutandis to a non-transitory computer readable medium that stores instructions that may be executed by the system.

Any reference in the specification to a non-transitory computer readable medium should be applied mutatis mutandis to a system capable of executing the instructions stored in the non-transitory computer readable medium and should be applied mutatis mutandis to method that may be executed by a computer that reads the instructions stored in the non-transitory computer readable medium.

Figure 1B:
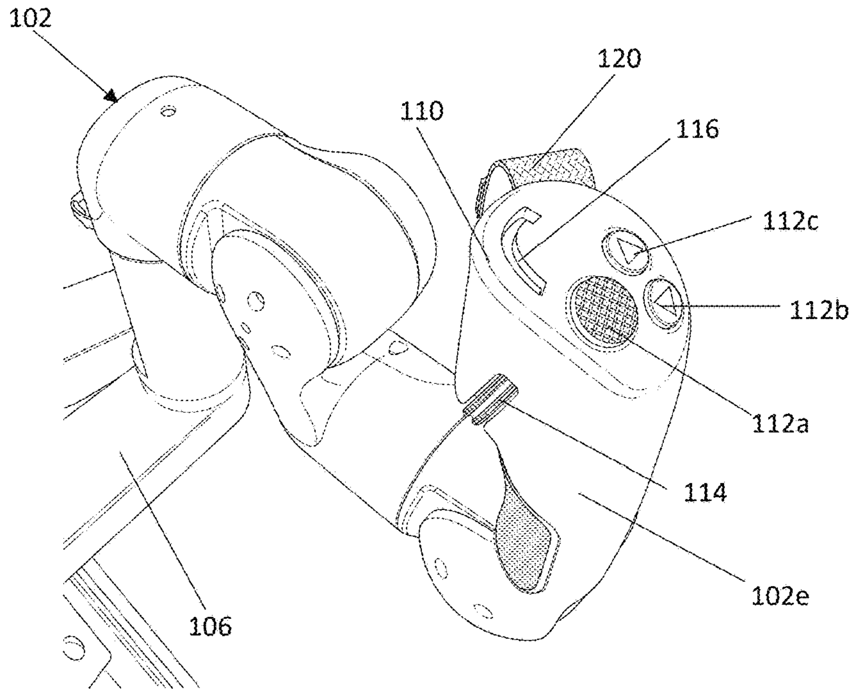
Figure 1C:
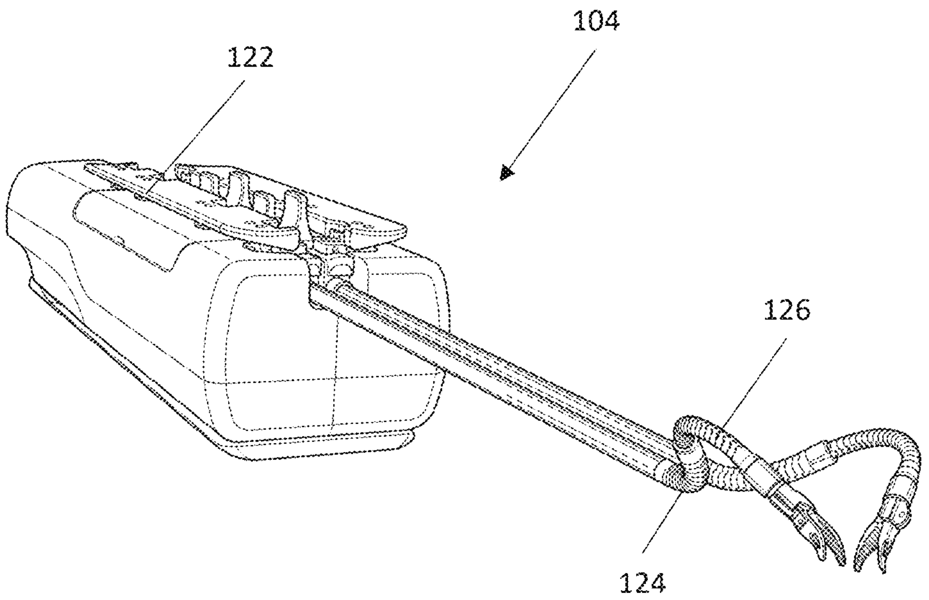

Bearing this in mind, attention is drawn to FIGS. 1A to 1C, showing schematic illustrations of components of a robotic system (also interchangeably referred to herein as "system") on which a control system for robotic systems operates, in accordance with the presently disclosed subject matter.

As shown in the schematic illustrations, robotic system 100 includes one or more input controls 102 (FIGS. 1A and 1B) and one or more respective mechanical arms 104 (FIG. 1C), such that each input control of the input controls 102 controls a respective mechanical arm of the mechanical arms 104. The one or more input controls 102 enable a user (e.g., a physician, surgeon, etc.) of the robotic system 100 to control the movement and operation of the one or more respective mechanical arms 104, during system's 100 operation, e.g., as the arms are at least partially inserted into the patient's body. It is to be noted that in some cases a single input control can control more than one mechanical arm, optionally divided by time, so that at each point in time the input control controls one mechanical arm that can optionally be selected by a user.

FIG. 1A shows a schematic illustration of an exemplary input control 102. As shown in the schematic illustration, the input control 102 may include a plurality of input control sections, sequentially coupled by a plurality of input control joints. The plurality of input control sections, which can be defined as rigid portions extending between two sequential joints, may include, for example, (a) a first segment 102*a* directed to enable mounting of the input control 102 to a platform 106 associated with a control console (not shown); (b) a second segment 102*b* coupled to the first segment 102*a* at a first joint 102*a-b*; (c) a third segment 102*c* coupled to the second segment 102*b* at a second joint 102*b-c*; (d) a fourth segment 102*d* coupled to the third segment 102*c* at a third joint 102*c-d*; and (e) a fifth segment 102*e* coupled to the fourth segment 102*d* at a fourth joint 102*d-e*, directed to function as a handle of the input control 102.

The fifth segment 102*e* may be shaped and sized to be gripped by a user's hand and/or by parts of the user's hand (e.g., by at least one finger) and may include: (a) a surface 108 (e.g., a concave surface) configured to be at least partially wrapped by the user's palm, and (b) a bulge 110, located at the surface's 108 distal end, configured to interact with the user's thumb, and optionally, one or more other fingers (e.g., the index finger, etc.), placed on or around the bulge 110.

Grasping at least a portion of the fifth segment 102*e* can enable the user (e.g., a physician, surgeon, and the like) to manipulate the movement of more than one section of the plurality of sections of the input control 102. For example, the user can maneuver the plurality of sections of the input control 102 by: (a) pulling the fifth segment 102*e* proximally towards him, (b) pushing the fifth segment 102*e* distally away from him, (c) moving the fifth segment 102*e* sideways, (d) directing the fifth segment 102*e* at any desired angle, etc. During these maneuvers, the relative position of adjacent input control sections, at the input control joint connecting them, can also change, as the input control joint can enable bending (flexion) of the adjacent input control sections relative to one another or rotation of the adjacent input control sections relative to each other.

In some cases, the input control joint can be further configured for locking, so as to prevent movement of adjacent input control sections relative to one another and maintain their last position (e.g., at the input control section's position measured and/or detected right before locking was applied, or the input control section's position measured and/or detected during the applying of locking). The locking of each input control joint can be independent of other input control joints, or can be performed simultaneously with all other input control joints (such as when entering "pause mode", as further detailed herein).

The input control 102 may further include one or more user interfaces, such as push button/s, slide button/s, scroll wheel/s, touch-sensitive button/s, LCD display/s, and the like, configured to control certain surgical functions and/or movements associated with the respective mechanical arm 104. The functions and/or movements may include, for example, (a) actuating linear movement of the respective mechanical arm 104 (i.e., direct back and forth movement of the respective mechanical arm 104); (b) actuating rotation of respective mechanical arm 104 portions; (c) actuating movement of a tool coupled to the distal end of the respective mechanical arm 104 (e.g., a gripper); (d) allowing selection of an operational mode of the input control 102 and/or of the respective mechanical arm 104 (e.g., "pause mode", "resume/active mode"), as will be explained hereafter, and the like.

For example, as seen in FIG. 1B, bulge 110 can include one or more of the following tactile push buttons: (a) button 112*a* for entering "pause mode", (b) button 112*b* for advancing the mechanical arm 104 linearly forwards, or (c) button 112*c* for retracting the mechanical arm 104 linearly backwards. The three tactile push buttons can be made of a material that improves friction contact with the user's hand (e.g., rubber) and can be mounted on the top surface of bulge 110 so as to be easily accessible and easily visible. In addition, bulge 110 can include one or more of: (d) a scroll knob 114 located at a bottom surface of bulge 110 configured to be engaged by the middle finger or thumb of the user; (e) a LED indicator 116 configured to change colors depending on the current operational mode of the input control 102 (e.g., blue light for "pause mode", green light for "active/resume mode", red for indicating an error or misalignment); or (f) a lever 118 including a loop 120, used for operating an end tool of the respective mechanical arm 104.

Turning to FIG. 1C, there is shown a schematic illustration of a pair of mechanical arms 104 extending from a motor unit 122, which houses one or more motors for driving movement of the pair of mechanical arms.

As shown in the schematic illustration, a mechanical arm 104, which can be at least partially inserted into a patient's natural orifice (e.g., vagina, rectum, mouth, nostril, and the like) during the system's 100 operation, may include a plurality of segments coupled to one another (e.g., by forming a series of segments that fit one another or slide through one another). Each of the plurality of segments, which may have flexible features, may be configured to imitate an angle between a respective pair of adjacent input control sections of the input control 102 (i.e., first segment 102*a*, second segment 102*b*, third segment 102*c*, fourth segment 102*d*, and fifth segment 102*e*), coupled by a respective input control joint of the input control 102 (i.e., first joint 102*a-b*, second joint 102*b-c*, third joint 102*c-d*, and fourth joint 102*d-e*). For example, as shown in FIG. 1C, each mechanical arm 104 of the pair of mechanical arms includes a first segment 124 and a second segment 126. The first segment 124 is configured to imitate the angle between the fourth segment 102*d* and the fifth segment 102*e*, coupled by fourth joint 102*d-e*, whereas the second segment 126 is configured to imitate the angle between the third segment 102*c* and the second segment 102*b*, coupled by third joint 102*b-c*.

In some cases, the number of segments of each mechanical arm 104 can be of at least the same number as the number of respective pairs of adjacent input control sections, coupled by input control, of the input controls 102 corresponding to the pair of mechanical arms 104, such that movement and/or position of input controls components (e.g., input control sections, input control joints) can be mapped to movement and/or position of corresponding mechanical arms segments.

In some cases, the mechanical arm 104 can define a humanoid structure, where segments of the mechanical arm are equivalent to those of a human arm, including, for example, a humerus section, a radius section, a shoulder joint, an elbow joint, and a wrist joint.

Attention is now drawn to the operation of the robotic system 100 described therebefore.

During the system's 100 operation, a user can move between several operational modes of the system, such as a "resume/active mode", a "pause mode", and an "upon resume mode".

In the "resume/active mode", the user grasps one or more input controls 102, for example, by placing his hand/s in contact with their respective handles (i.e., the fifth segment 102*e*), and maneuvers them to control the movement of one or more mechanical arms 104, inserted at least partially into a patient's body. During this mode, every maneuver performed by the user on the one or more input controls 102 is followed by an appropriate movement of the respective one or more mechanical arms 104. The execution of the appropriate movement can be performed, for example, in real-time or in near real-time, where the movement is delayed by a certain time gap (such as, a few milliseconds) required for the system 100 in order to process and complete the operation.

Once the user decides to move to "pause mode", e.g., since the user wants to rest his hand/s, decide on his next move, and the like, the user can actuate an interface of the one or more input controls 102, for example, by pushing a respective "pause" button 112*a*, to maintain the one or more input controls 102 and their respective one or more mechanical arms 104 in their current configuration (which will be explained in detail hereafter).

Maintaining the one or more input controls 102 in their current configuration can be achieved, for example, by locking at least one and optionally all of their input control joints to prevent any bending and/or rotation at the joints. The locking can be performed, for example, by corresponding brakes (e.g., electromagnetic brakes), such that upon entering "pause mode" (e.g., upon pressing of the respective "pause" button) electrical supply to the respective brakes is ceased, causing the brakes to restrict or prevent movement of the input control joints.

As the user decides to exit the "pause mode" and return to "resume/active mode", the user may replace his hand/s in contact with the handles of the input controls 102 (e.g., fifth segment 102) and wait for the system's entry back to "resume/active mode". This mode is known as "upon resume mode".

In some cases, further to the placement of the hand/s in contact with the handles, the user may need to actuate an input control interface, for example, by squeezing a lever, as described herein, in order to return to the "resume/active mode". The squeezing of the lever can reestablish electrical supply to the corresponding brakes of the input control joints, which releases the brakes and unlocks the input control joints.

During "pause mode" or "upon resume mode", a misalignment between the one or more input controls 102 and their respective one or more mechanical arms 104 can occur, which may prevent system 100 from reentering "resume/active mode". Misalignment can be defined as a scenario in which the configurations of the one or more input controls 102 and their respective one or more mechanical arms 104 are not aligned, as they should be during a proper operation of the system 100. Misalignment can be a result of one or more of the following: (a) an object (e.g., a tissue) contacting one or more of mechanical arms 104, preventing them from moving, while their respective one or more input controls 102 are still in motion; (b) movement of the one or more mechanical arms 104 independently of their respective one or more input controls 102; (c) physical movement limitations associated with the one or more mechanical arms 104; (d) movement of the one or more input controls 102 while in pause mode; (e) use of an emergency button associated with the one or more input controls 102 and their respective one or more mechanical arms 104; (f) misalignment originated from the initial configurations of the at least one input control and the at least one mechanical arm; (g) one or more mechanical arm malfunctions; etc.

Misalignments, such as those mentioned hereinbefore, are identified and attended to by a control system for robotic systems of the presently disclosed subject matter, as further detailed herein, inter alia, with reference to FIGS. 2-3 and 4A-4H.

Attention is now drawn to a description of the components of the control system for robotic systems 200.

FIG. 2 is a block diagram schematically illustrating one example of the control system for robotic systems 200, in accordance with the presently disclosed subject matter.

In accordance with the presently disclosed subject matter, the control system for robotic systems 200 (also interchangeably referred to herein as "system 200") can comprise a network interface 206. The network interface 206 (e.g., a network card, a Wi-Fi client, a Li-Fi client, 3G/4G client, or any other component), enables system 200 to communicate over a network with external systems and handles inbound and outbound communications from such systems. For example, system 200 can receive, through network interface 206, the configurations of: (a) one or more input controls and (b) their respective one or more mechanical arms.

System 200 can further comprise or be otherwise associated with a data repository 204 (e.g., a database, a storage system, a memory including Read Only Memory—ROM, Random Access Memory-RAM, or any other type of memory, etc.) configured to store data. Some examples of data that can be stored in the data repository 204 include:

Types of misalignments;

Actions associated with different types of misalignments;

Input control configurations;

Mechanical arm configurations;

Angles of one or more input control joints;

Various thresholds (e.g., low threshold, high threshold); etc.

Data repository 204 can be further configured to enable retrieval and/or update and/or deletion of the stored data. It is to be noted that in some cases, data repository 204 can be distributed, while the system 200 has access to the information stored thereon, e.g., via a wired or wireless network to which system 200 is able to connect (utilizing its network interface 206).

System 200 further comprises processing circuitry 202. Processing circuitry 202 can be one or more processing units (e.g., central processing units), microprocessors, microcontrollers (e.g., microcontroller units (MCUs)) or any other computing devices or modules, including multiple and/or parallel and/or distributed processing units, which are adapted to independently or cooperatively process data for controlling relevant system 200 resources and for enabling operations related to system's 200 resources.

The processing circuitry 202 comprises a misalignment identification and/or correction module 208, configured to perform a misalignment identification and/or correction process, as further detailed herein, inter alia with reference to FIG. 3.

Turning to FIG. 3 there is shown a flowchart illustrating one example of operations carried out by the control system for robotic systems 200, in accordance with the presently disclosed subject matter.

Accordingly, the control system for robotic systems 200 (also interchangeably referred to hereafter as "system 200") can be configured to perform a misalignment identification and/or correction process 300, e.g., using misalignment identification and/or correction module 208.

For this purpose, system 200 obtains: (a) a current input control configuration of at least one input control 102, and (b) a current mechanical arm configuration of its respective at least one mechanical arm 104 (block 302). The current configurations can be received from an external source or be determined internally, e.g., by the processing circuitry 202. The current configuration of the at least one input control 102 can be determined, for example, by its one or more input control angles, which are angles between two adjacent sections of the plurality of input control sections of the input control 102, coupled by an input control joint, whereas the current configuration of its respective at least one mechanical arm 104 can be determined, for example, by angles imitated by its one or more segments. For example, the configurations of an input control 102, composed of four input control sections and three input control joints having angles of 120°, 60°, and 120°, and of its respective mechanical arm 104, composed of three segments imitating angles of 122°, 62°, and 120°, are determined based on all three angles.

It is to be noted that, in some cases, the current configuration of the at least one mechanical arm can be determined by: (a) measuring a tension found on at least one cable connecting the mechanical arm to a respective motor (e.g., the motor found in motor unit 122), or (b) measuring the operation of the respective motor.

Figure 4A:
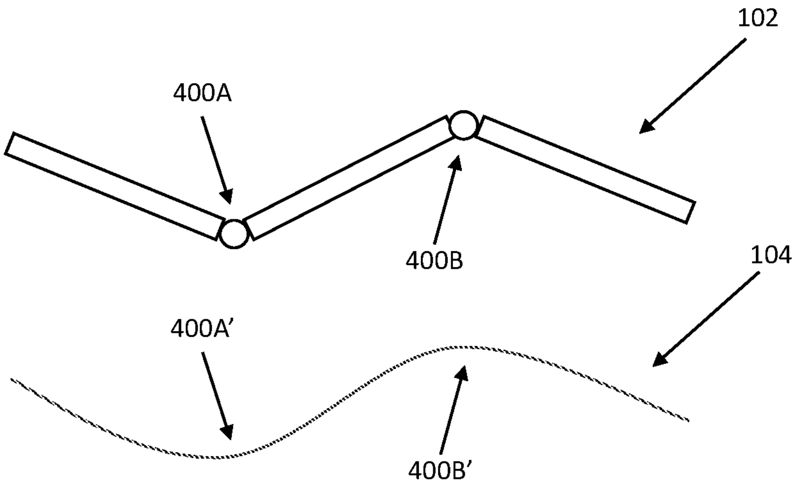
FIGS. 4A-4H are schematic illustrations of misalignments between components of a robotic system on which a control system for robotic systems operates, in accordance with the presently disclosed subject matter; and, FIG. 5 is a flowchart illustrating another example of a sequence of operations carried out by a control system for robotic systems, in accordance with the presently disclosed subject matter.

Once the current configurations of the at least one input control 102 and its respective at least one mechanical arm 104 are obtained, system 200 identifies a misalignment by comparing the configurations (block 304). It is to be noted that during a proper operation of system 200 the configurations of the at least one input control 102 and its respective at least one mechanical arm 104 should be aligned (as shown in FIG. 4A), and as such, a misalignment between the configurations should not be identified.

In some cases, the misalignment can be identified upon one or more pairs of respective angles of the one or more input control angles and the one or more angles imitated by respective segments of the one or more mechanical arms meeting a misalignment condition. The misalignment condition can be, for example, that a difference between the respective angles exceeds a tolerance threshold (i.e., a threshold distance between to respective angles) or that the respective angles are not equal. For example, in accordance with the example described therebefore, system 200 detects that two of the three input control angles of the input control 102 are not equal and/or are not within a threshold distance from their respective angles imitated by their respective segments of the mechanical arm 104, and as a result, identifies a misalignment between the two.

Figure 4B:
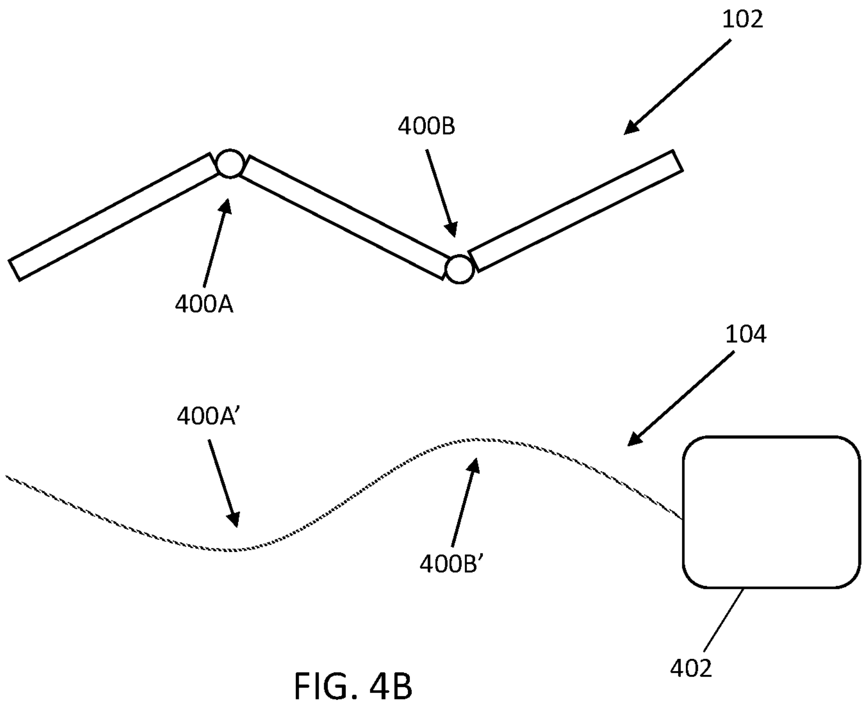

In some cases, the misalignment between the at least one input control 102 and its respective at least one mechanical arm 104 can be a consequence of a scenario in which the at least one mechanical arm 104 is in contact with an object preventing it from moving further, while the at least one input control 102 is still in motion. For example, as illustrated in FIG. 4B, the at least one mechanical arm 104 can be in contact with a tissue 402 preventing it from moving further, while the at least one input control 102 moves past the tissue location. As a result, the configuration of the input control 102, determined by its input control angles, denoted 400A and 400B, and the configuration of the mechanical arm 104, determined by the angles imitated by its respective segments, denoted 400A' and 400B', are not aligned.

Figure 4C:
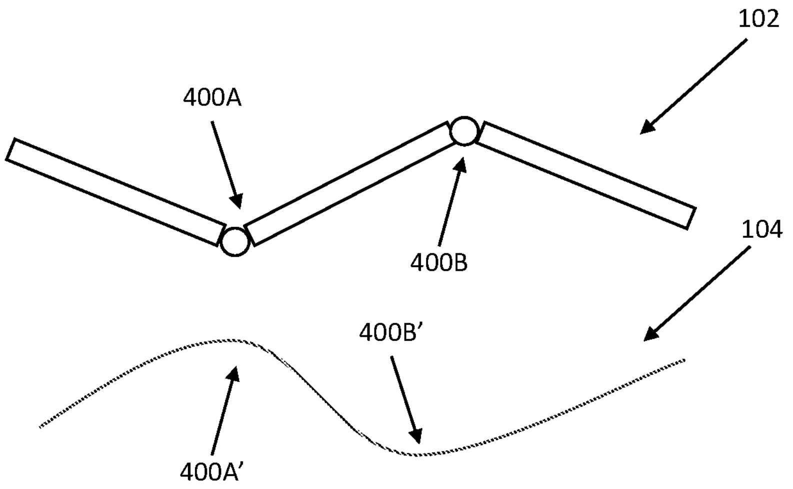
Figure 4D:
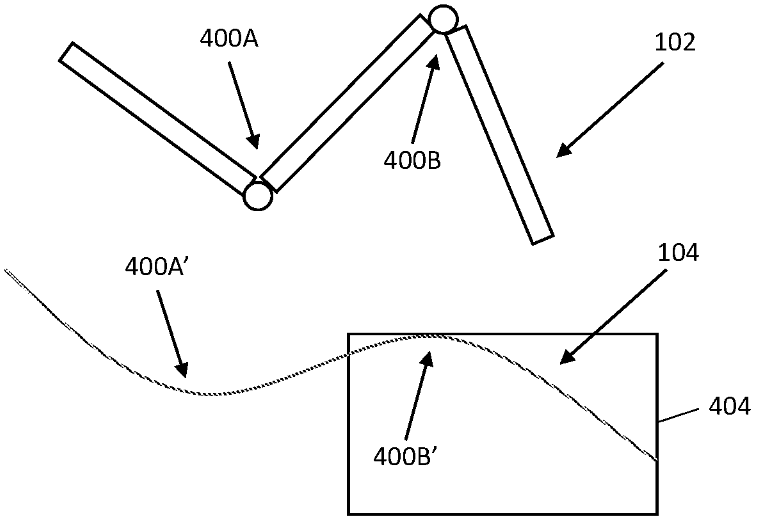

In some cases, the misalignment between the at least one input control 102 and its respective at least one mechanical arm 104 can be a consequence of a scenario in which the at least one mechanical arm 104 moves independently of the at least one input control 102. For example, as illustrated in FIG. 4C, due to an arm malfunction, the at least one mechanical arm 104 is still in motion, while the at least one input control 102 is in "pause mode". As a result, the configuration of the input control 102, determined by its input control angles, denoted 400A and 400B, and the configuration of the mechanical arm 104, determined by the angles imitated by its respective segments, denoted 400A' and 400B', are not aligned.

In some cases, the misalignment between the at least one input control 102 and its respective at least one mechanical arm 104 can be a consequence of a scenario in which there are physical movement limitations associated with the operation of the at least one mechanical arm 104. For example, as illustrated on FIG. 4D, the at least one mechanical arm 104 is physically limited by organ space 404, in which it is inserted, while the one input control has at least 102 free to move in space, without having the same limitation being imposed on it. As a result, the configuration of the input control 102, determined by its input control angles, denoted 400A and 400B, and the configuration of the mechanical arm 104, determined by the angles imitated by its respective segments, denoted 400A' and 400B', are not aligned.

Figure 4E:
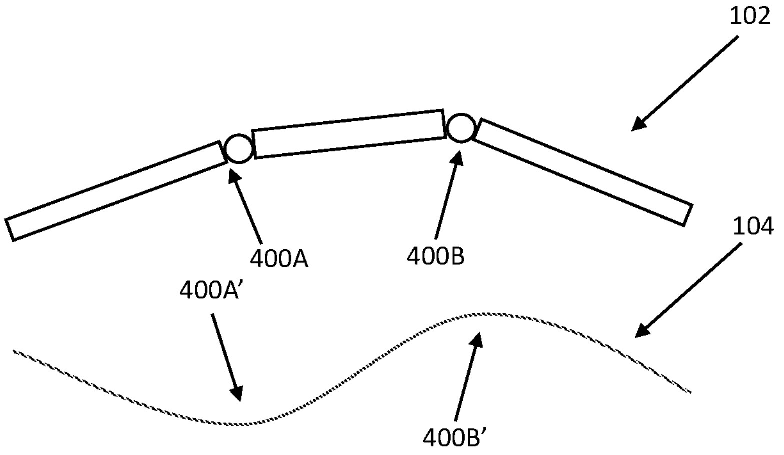

In some cases, the misalignment between the at least one input control 102 and its respective at least one mechanical arm 104 can be a consequence of a scenario in which there is an unintentional movement of the at least one input control 102, while in a pause mode. For example, as illustrated in FIG. 4E, while in "pause mode", the at least one input control 102 is shifted from its present configuration in response to unintentional contact caused, for instance, by the user operating the system 100. As a result, the configuration of the input control 102, determined by its input control angles, denoted 400A and 400B, and the configuration of the mechanical arm 104, determined by the angles imitated by its respective segments, denoted 400A' and 400B', are not aligned.

Figure 4F:
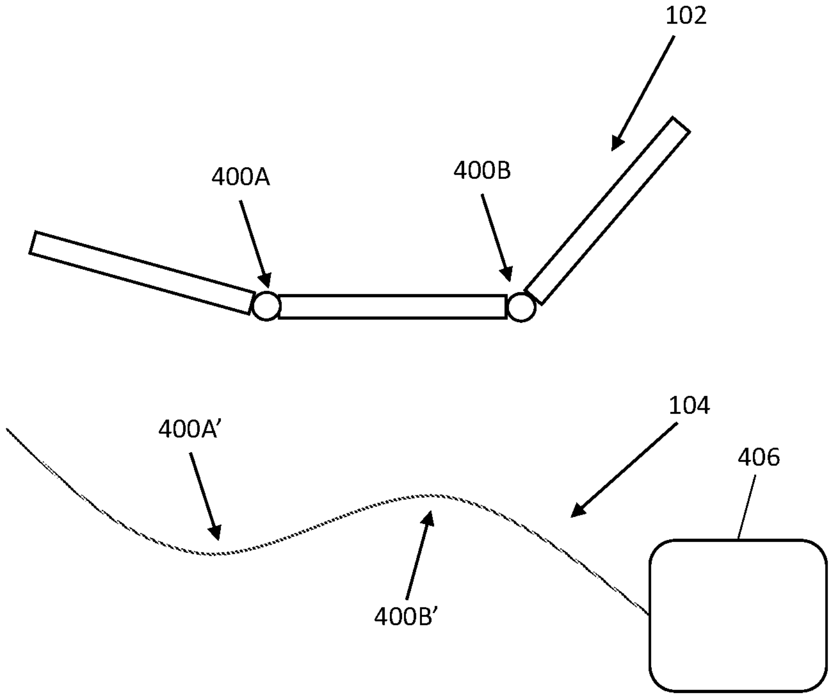

In some cases, the misalignment between the at least one input control 102 and its respective at least one mechanical arm 104 can be a consequence of a scenario in which an emergency button, configured to implement instant shutdown of the system 100, is being pressed. Upon pressing of the emergency button, the at least one input control 102 and its respective at least one mechanical arm 104 are configured to maintain their configuration. For example, as illustrated in FIG. 4F, the emergency button is pressed after the at least one mechanical arm 104 has been in contact with a tissue 406 preventing it from moving further for 20 seconds, while the at least one input control 102 was free to move in space during that time. As a result, at the moment of pressing, the configurations of the at least one input control 102 and its respective at least one mechanical arm 104 are not aligned.

Figure 4G:
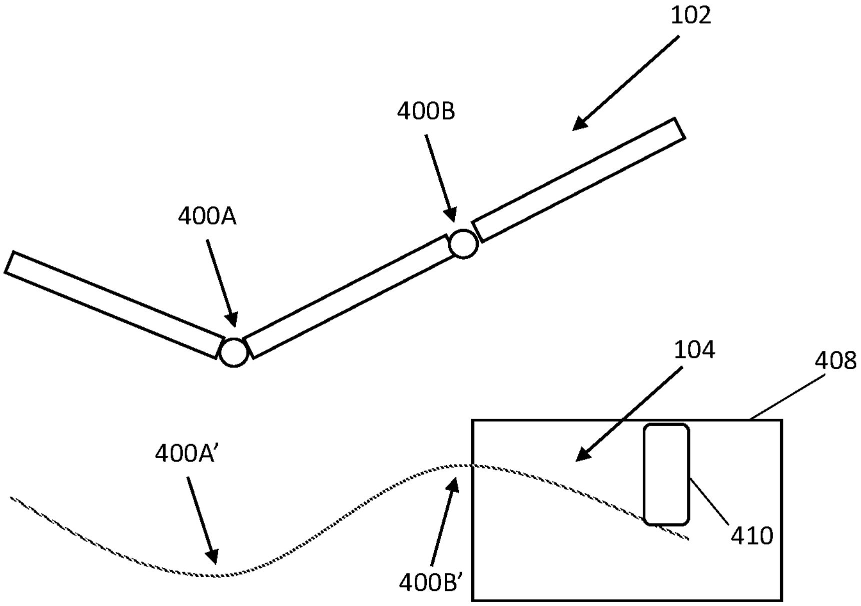

In some cases, the misalignment between the at least one input control 102 and its respective at least one mechanical arm 104 can be a consequence of a scenario in which the initial configurations of the at least one input control 102 and the at least one mechanical arm 104 are not aligned. For example, as illustrated in FIG. 4G, while inserting the at least one mechanical arm 104 into an organ cavity 408, the at least one mechanical arm 104 cannot enter its initial configuration, as there is an unknown tissue 410 that prevents it from doing so. As a result, the initial configuration of the at least one mechanical arm 104 is not aligned with the initial configuration of the at least one input control 102, since the at least one input control 102 is not affected by the limitation imposed by the unknown tissue.

Figure 4H:
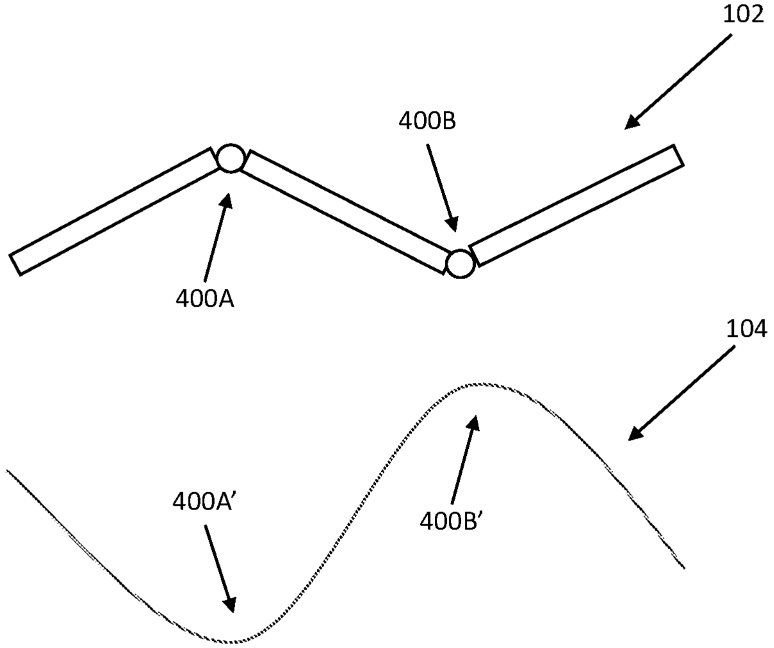

In some cases, the misalignment between the at least one input control 102 and its respective at least one mechanical arm 104 can be a consequence of a scenario involving at least one arm malfunction. For example, as illustrated in FIG. 4H, during the operation of system 100, the at least one mechanical arm 104 stops responding to commands given to it by the at least one input control 102 and is fixed in place. As a result, the configuration of the input control 102, determined by its input control angles, denoted 400A and 400B, and the configuration of the mechanical arm 104, determined by the angles imitated by its respective segments, denoted 400A' and 400B', are not aligned.

Upon identification of the misalignment, system 200 performs an action (block 306). The action may include, for example, one or more of: (a) providing a user of the system with an indication of the misalignment (e.g., an alert (visual, hepatic, sound, and the like)), (b) causing movement of at least one segment of the at least one mechanical arm 104 to at least reduce the misalignment between the current input control configuration and the current mechanical arm configuration, or (c) instructing the user to move at least one joint of the at least one input control 102 to at least reduce the misalignment between the current input control configuration and the current mechanical arm configuration. For example, in accordance with the example described therebefore, upon identification of the misalignment between the current configurations of the input control 102 and its respective mechanical arm 104, system 200 provides a user of the system with an indication of the misalignment.

In some cases, the action can be selected based on a type of tool coupled to a distal end of the at least one mechanical arm 104. For example, the tool can be a cutting tool (e.g., scissors), the use of which requires a delicate and precise action, a grabbing tool, the use of which enables a coarser action, or any other tool used to perform the surgical action, during the system's 100 operation.

In some cases, the action further includes providing haptic feedback using a haptic feedback mechanism located within the at least one input control 102.

In some cases, where the action performed by system 200 is causing movement of the at least one segment of the at least one mechanical arm 104, the movement is performed upon an angular difference between the at least one input control 102 and its respective at least one mechanical arm 104 being above a low threshold and below a high threshold. The angular difference can be determined based on at least one joint angular difference, which is the angular difference between at least one input control joint and its respective at least one segment. For example, in accordance with the example described therebefore, the angular differences between the input control angles and the angles imitated by their respective segments are 5°. 2°, and 0°.

In other cases, where the action performed by system 200 is providing a user of the system with an indication of the misalignment, the indication is provided upon the angular difference between the at least one input control and its respective at least one mechanical arm being above a low threshold.

In addition to identifying a misalignment between at least one input control and its respective at least one mechanical arm, system 200 can be further utilized to identify a misalignment between current and previous configurations of at least one input control 102, as further detailed herein, inter alia with reference to FIG. 5.

FIG. 5 shows a flowchart illustrating another example of operations carried out by the control system for robotic systems 200, in accordance with the presently disclosed subject matter.

Accordingly, the control system for robotic systems 200 (also interchangeably referred to hereafter as "system 200") can be configured to perform a misalignment identification and/or correction process 500, e.g., using misalignment identification and/or correction module 208.

For this purpose, system 200 obtains: (a) a previous input control configuration of at least one input control 102, and (b) a current input control configuration of the at least one input control 102 (block 502). The previous and current configurations can be defined by one or more input control angles, which are angles between two adjacent sections of the plurality of input control sections of the at least one input control 102, coupled by an input control joint. For example, the previous and current configurations of an input control 102, composed of four input control sections and three input control joints, are determined based on the angles of its three input control joints. The angles of the three input control joints of the input control 102 in its previous configuration are 120°, 60°, and 120°, whereas the angles of the three input control joints of the input control 102 in its current configuration are 122°, 55°, 120°.

Once the previous and current input control configurations are obtained, system 200 identifies a misalignment by comparing the configurations (block 504). In some cases, the misalignment can be identified upon any pair of respective angles of the previous and current configurations meeting a misalignment condition. The misalignment condition can be, for example, that a difference between the respective angles exceeds a tolerance threshold, or that the angles of the pair are not equal. For example, in accordance with the example described therebefore, system 200 identifies that two of the three input control angles of the input control 102 in its current configuration are not equal to their respective input control angles of the input control 102 in its previous configuration, and as a result, identifies a misalignment between the two.

Upon identification of the misalignment, system 200 performs an action (block 506). The action may include, for example, one or more of: (a) providing a user of the system with an indication of the misalignment, or (b) instructing the user to move at least one joint of the at least one input control 102 to at least reduce the misalignment between the current input control configuration and the previous input control configuration. For example, in accordance with the example described therebefore, upon identification of the misalignment between the current and previous configurations of the input control 102, system 200 provides a user of the system with an indication of the misalignment.

In some cases, the identification of the misalignment and the performing of the action are performed when the at least one input control 102 is in "pause mode" or "upon resume mode", in which it is configured to maintain its configuration.

In some cases, the action further includes providing haptic feedback using a haptic feedback mechanism located within the at least one input control 102.

It is to be noted, with reference to FIGS. 3 and 5, that some of the blocks can be integrated into a consolidated block or can be broken down to a few blocks and/or other blocks may be added. It is to be further noted that some of the blocks are optional. It should be also noted that whilst the flow diagram is described also with reference to the system elements that realizes them, this is by no means binding, and the blocks can be performed by elements other than those described herein.

It is to be understood that the presently disclosed subject matter is not limited in its application to the details set forth in the description contained herein or illustrated in the drawings. The presently disclosed subject matter is capable of other embodiments and of being practiced and carried out in various ways. Hence, it is to be understood that the phraseology and terminology employed herein are for the purpose of description and should not be regarded as limiting. As such, those skilled in the art will appreciate that the conception upon which this disclosure is based may readily be utilized as a basis for designing other structures, methods, and systems for carrying out the several purposes of the present presently disclosed subject matter.

It will also be understood that the system according to the presently disclosed subject matter can be implemented, at least partly, as a suitably programmed computer. Likewise, the presently disclosed subject matter contemplates a computer program being readable by a computer for executing the disclosed method. The presently disclosed subject matter further contemplates a machine-readable memory tangibly embodying a program of instructions executable by the machine for executing the disclosed method.

The invention claimed is:

1. A control system for a robotic system consisting of one or more input controls, each including a plurality of input control sections sequentially coupled by input control joints, and one or more mechanical arms, each associated with a respective input control of the one or more input controls and includes a plurality of segments coupled to one another, wherein each segment is configured to imitate an angle of a respective pair of input control sections, coupled by an input control joint, the control system comprising a processing circuitry configured to:

obtain:

(a) a current input control configuration of at least one input control of the one or more input controls, and (b) a current mechanical arm configuration of at least one mechanical arm of the one or more mechanical arms;

wherein: (i) one or more segments of the plurality of segments define the current mechanical arm configuration, and (ii) one or more input control angles of one or more input control joints of the input control joints define the current input control configuration;

identify a misalignment between at least one input control of the one or more input controls and its respective at least one mechanical arm of the one or more mechanical arms by comparing the current input control configuration and the current mechanical arm configuration of the at least one input control of the one or more input controls and its respective at least one mechanical arm of the one or more mechanical arms; and, upon identification of the misalignment, perform an action.

2. The system of claim 1, wherein the action includes one or more of: (a) providing a user of the system with an indication of the misalignment, (b) causing movement of at least one segment of the at least one mechanical arm to at least reduce the misalignment between the current input control configuration of said input control and the current mechanical arm configuration of the mechanical arm, or (c) instructing the user to move at least one joint of the at least one input control to at least reduce the misalignment between the current input control configuration of said input control and the current mechanical arm configuration of said mechanical arm.

3. The system of claim 1, wherein the identify and the perform operations are performed when the at least one input control of the one or more input controls and its respective at least one mechanical arm of the one or more mechanical arms are in a pause or upon resume mode, in which the input control and the mechanical arm are configured to maintain their configuration.

4. The system of claim 1, wherein each input control angle of the one or more input control angles of the at least one input control is an angle between two adjacent sections of the plurality of input control sections, coupled by an input control joint of the input control joints.

5. The system of claim 1, wherein the configuration of the at least one mechanical arm is determined by measuring the operation of a respective motor connected to the at least one mechanical arm.

6. The system of claim 1, wherein the misalignment between the at least one input control of the one or more input controls and its respective at least one mechanical arm of the one or more mechanical arms is identified upon any pair of respective angles of the one or more input control angles and the one or more angles imitated by respective segments of the one or more mechanical arms meeting a misalignment condition.

7. The system of claim 6, wherein the misalignment condition is that a difference between the respective angles exceeds a tolerance threshold, or that the angles of the pair are not equal.

8. The system of claim 1, wherein the action is causing movement of the at least one segment, and wherein the movement is performed upon an angular difference between the at least one input control and its respective at least one mechanical arm being above a low threshold and below a high threshold.

9. The system of claim 1, wherein the action is selected from a plurality of possible actions based on a type of tool coupled to a distal end of the at least one mechanical arm.

10. The system of claim 1, wherein the action includes providing haptic feedback using a haptic feedback mechanism comprised within the at least one input control.

11. The system of claim 1, wherein the misalignment between the at least one input control of the one or more input controls and its respective at least one mechanical arm of the one or more mechanical arms is due to any one of the following:

(a) the at least one mechanical arm contacting an object preventing the mechanical arm from moving further, while the input control is still in motion;

(b) movement of the at least one mechanical arm independently of the at least one input control;

(c) physical movement limitations associated with the at least one mechanical arm;

(d) movement of the at least one input control while in a pause mode;

(e) use of an emergency button associated with the at least one input control and its respective at least one mechanical arm, wherein upon pressing of the emergency button the at least one input control and its respective at least one mechanical arm are configured to maintain their configuration;

(f) an initial configuration of the at least one input control and the at least one mechanical arm;

(g) one or more arm malfunctions.

12. The system of claim 11, wherein the object is a tissue.

13. A control system for a robotic system including one or more input controls, each including a plurality of input control sections sequentially coupled by input control joints, the control system comprising a processing circuitry configured to:

obtain:

(a) a previous input control configuration of at least one input control of the one or more input controls, and (b) a current input control configuration of said at least one input control;

wherein each configuration of said at least one input control is defined by one or more input control angles of the one or more input control joints of the input control joints;

identify a misalignment between the previous input control configuration and the current input control configuration of said at least one mechanical arm by comparing the configurations; and, upon identification of the misalignment, perform an action.

14. The system of claim 13, wherein the action includes one or more of: (a) providing a user of the system with an indication of the misalignment, or (b) instructing the user to move at least one joint of the at least one input control to at least reduce the misalignment between the current input control configuration of said input control and the previous input control configuration of said input control.

15. The system of claim 13, wherein the identify and the perform operations are performed when the at least one input control is in a pause or upon resume mode in which the input control is configured to maintain its configuration.

16. The system of claim 13, wherein each input control angle of the one or more input control angles of the at least one input control is an angle between two adjacent sections of the plurality of input control sections, coupled by an input control joint of the input control joints.

17. The system of claim 13, wherein the misalignment between the previous and current configurations of the at least one input control of the one or more input controls is identified upon any pair of respective angles of the previous and current configurations meeting a misalignment condition.

18. The system of claim 17, wherein the misalignment condition is that a difference between the angles of the pair exceed a tolerance threshold, or that the angles of the pair are not equal.

19. The system of claim 13, wherein the action includes providing haptic feedback using a haptic feedback mechanism comprised within the at least one input control.

20. A control method for a robotic system consisting of one or more input controls, each including a plurality of input control sections sequentially coupled by input control joints, and one or more mechanical arms, each associated with a respective input control of the one or more input controls and includes a plurality of segments coupled to one another, wherein each segment is configured to imitate an angle of a respective pair of input control sections, coupled by an input control joint, the control method comprising:

obtaining:

(a) a current input control configuration of at least one input control of the one or more input controls, and (b) a current mechanical arm configuration of at least one mechanical arm of the one or more mechanical arms;

wherein: (i) one or more segments of the plurality of segments define the current mechanical arm configuration, and (ii) one or more input control angles of one or more input control joints of the input control joints define the current input control configuration;

identifying a misalignment between at least one input control of the one or more input controls and its respective at least one mechanical arm of the one or more mechanical arms by comparing the current input control configuration and the current mechanical arm configuration of the at least one input control of the one or more input controls and its respective at least one mechanical arm of the one or more mechanical arms; and, upon identification of the misalignment, performing an action.

21. A non-transitory computer readable storage medium having computer readable program code embodied therewith, the computer readable program code, executable by at least one processor to perform a control method, the method comprising:

obtaining:

(a) a current input control configuration of at least one input control of the-one or more input controls, and (b) a current mechanical arm configuration of at least one mechanical arm of the one or more mechanical arms;

wherein: (i) one or more segments of a plurality of segments define the current mechanical arm configuration, and (ii) one or more input control angles of one or more input control joints of a plurality of input control joints define the current input control configuration;

identifying a misalignment between at least one input control of the one or more input controls and its respective at least one mechanical arm of the one or more mechanical arms by comparing the current input control configuration and the current mechanical arm configuration of the at least one input control of the one or more input controls and its respective at least one mechanical arm of the one or more mechanical arms; and, upon identification of the misalignment, performing an action.

* * * * *